United States Patent [19]

Takagishi et al.

[11] 4,339,463
[45] Jul. 13, 1982

[54] ENTEROSOLUBLE HARD-CAPSULATED MEDICAMENTS

[75] Inventors: Yasushi Takagishi, Nishinomiya; Yoshio Doi, Ibaraki; Noboru Hoshi, Kigashi-Kurume, all of Japan

[73] Assignees: Shionogi & Co., Ltd., Osaka; Shin-Etsu Chemical Co., Ltd., Tokyo, both of Japan

[21] Appl. No.: 169,395

[22] Filed: Jul. 16, 1980

[30] Foreign Application Priority Data

Aug. 24, 1979 [JP] Japan .................................. 54-108447

[51] Int. Cl.³ ........................ A61K 9/48; A61K 47/00
[52] U.S. Cl. ......................................... 424/35; 424/4; 424/21; 424/38
[58] Field of Search ............................... 424/4, 19–22, 424/32–38, 4

[56] References Cited

U.S. PATENT DOCUMENTS

| 2,349,430 | 5/1944 | Hiatt et al. ............................. 424/35 |
| 2,491,475 | 12/1949 | Bogin ..................................... 424/21 |
| 2,718,667 | 9/1955 | Malm et al. ........................ 424/35 X |
| 2,801,203 | 7/1957 | Leb et al. .................................. 424/4 |
| 3,017,329 | 1/1962 | Dulmage ................................. 424/4 |
| 3,056,724 | 10/1962 | Marston ................................. 424/22 |
| 3,341,417 | 9/1967 | Sinaiko ................................... 424/4 |
| 3,444,290 | 5/1969 | Wai ......................................... 424/4 |
| 3,507,952 | 4/1970 | Rednick et al. ........................ 424/22 |
| 3,535,419 | 10/1970 | Siegrist et al. ........................ 424/22 |
| 3,574,820 | 4/1971 | Johnson et al. ........................ 424/22 |
| 3,656,997 | 4/1972 | Cordes ............................... 424/35 X |
| 3,823,228 | 7/1974 | Ferris et al. ............................. 424/4 |
| 3,927,195 | 12/1975 | Messora ................................. 424/21 |
| 3,976,764 | 8/1976 | Watanabe et al. .................... 424/19 |
| 4,126,672 | 11/1978 | Sheth et al. ........................... 424/22 |
| 4,138,013 | 2/1979 | Okajima ................................. 424/35 |
| 4,193,985 | 3/1980 | Bechgaard et al. ..................... 424/4 |

Primary Examiner—Shep K. Rose
Attorney, Agent, or Firm—Toren, McGeady & Stanger

[57] ABSTRACT

The invention provides a novel means for overcoming the problem of undue and irregular delay in the exhibition of the effect of medicine when a patient is administrated with an enterosoluble hard-capsulated medicament. The unexpected discovery that the key parameter ruling the smooth transfer of an enterosoluble capsule from the stomach to the intestinal canals is the overall specific gravity of the capsule has led to the establishment of the invention which proposes an enterosoluble hard-capsulated medicament having an overall specific gravity of at least 1.05 or, preferably, at least 1.10.

2 Claims, 5 Drawing Figures

| Subject | Lapse of time after administration, minutes | | | |
|---|---|---|---|---|
| | 20 | 35 | 50 | 90 |
| H.Y. |  |  |  |  |
| N.H. |  |  |  |  |
| Y.T. |  |  |  |  |
| Y.D. |  |  |  |  |

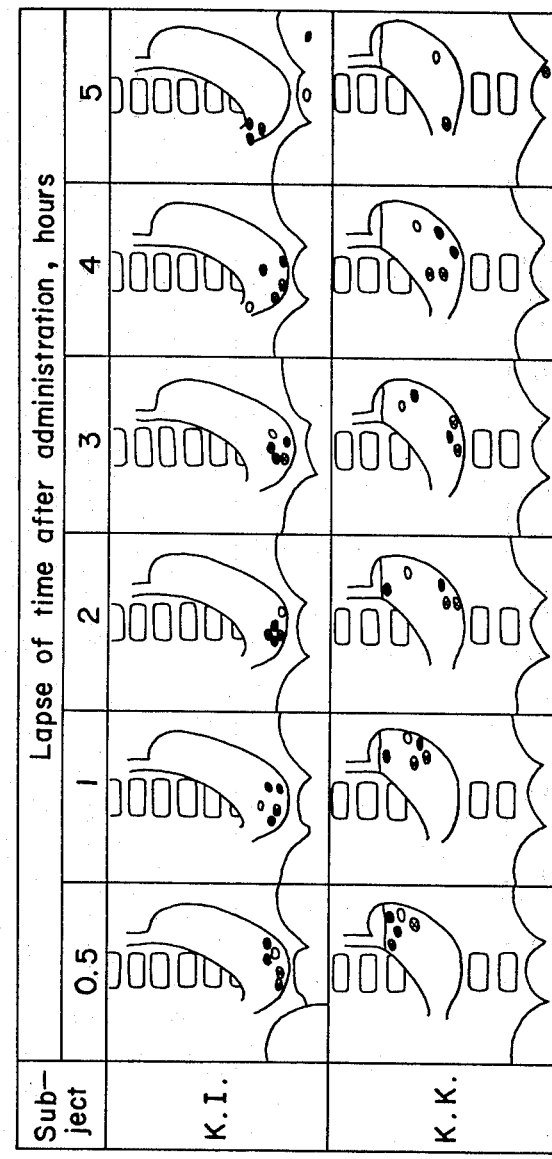

ENTEROSOLUBLE HARD-CAPSULATED MEDICAMENTS

BACKGROUND OF THE INVENTION

The present invention relates to an improved enterosoluble hard capsule containing a medicament.

As may be needless to say, what is meant by the term of enterosoluble medicamental hard capsule is, as the first meaning, a capsulated drug form orally administrated which is expected to release the active ingredient contained therein only when it has arrived at the intestinal canals. Along with the enterosoluble tablets, enterosoluble medicamental hard capsules belong to a class of enterosoluble medicaments and are widely used owing to the secondary effects of preventing inactivation of the active ingredient by the gastric juice and preventing troubles of and digestion impediment in the stomach by the ingredient as well as increasing the effective concentration of the active ingredient in the intestinal canals and extending the effective time of the ingredient.

Enterosoluble medicamental hard capsules are usually prepared by providing enterosoluble coating films on to the surface of a hard capsule for medicament use made of gelatine or the like which has been sealed after filling with a desired medicamental ingredient. The film-forming enterosoluble substances used in the above coating include copolymers of unsaturated carboxylic acids such as copolymers of methacrylic acid and methyl methacrylate and phthalic acid or succinic acid esters of certain cellulose derivatives such as cellulose acetate phthalate, hydroxypropylmethylcellulose phthalate, methylcellulose phthalate, cellulose acetate succinate and the like.

An alternative way for rendering a gelatine hard capsule enterosoluble is a method in which the outer surface of the gelatine capsule is treated with formalin so as that the solubility of the capsule in the gastric juice is decreased.

Both of the above described methods utilize the principle of imparting enteric solubility to the outer surface of an inherently gastrosoluble gelatine hard capsule by a secondary treatment. These methods have, accordingly, several defective points not only in the complicated process of the secondary treatment but also in the somewhat doubtful effectiveness of the enterosolubility imparted by the treatment. For example, the enterosoluble coating films formed on the surface of the gelatine capsules suffer from incomplete adhesive bonding between the enterosoluble coating films and the gelatine surface as well as gradual loss of the enterosolubility performance in the lapse of time, probably, due to the hydrolysis or other undesirable reaction which the enterosoluble substance undergoes with the moisture contained in the gelatine.

Further, the method of decreasing the solubility of gelatine by the formalin treatment is a delicate process so that a desired degree of enterosolubility is obtained with extreme difficulties even with a most careful process control.

It has been recently proposed that hard capsules are shaped with a substance which in itself is enterosoluble as exemplified by the above named copolymers or cellulose derivatives for enterosoluble coating films. These capsules made of an enterosoluble substance are promising from the practical standpoint since enterosoluble capsulated medicaments can be prepared by merely filling the capsule with the desired active ingredient without the necessity of the secondary treatment although there are several remaining problems in the enterosoluble capsules of this type with respect to the fragility and insufficient flexibility of the capsule shells and the toxicity of the additives such as a plasticizer usually incorporated in the capsule materials.

Despite the very wide prevalence of administrating patients with enterosoluble capsulated medicaments with a therapeutic purpose, it is very often experienced in the actual clinic treatment that the exhibition of the effectiveness of the active ingredient contained in the enterosoluble hard capsules is unduly or irregularly delayed for an unknown reason so that the expected effect of the medicine in therapy or protection is obtained insufficiently or only with great variation in the effectiveness. This undesirable phenomenon of delayed exhibition of the effect of medicine appears not only in the case of administration after meal but also in the case of administration before meal.

SUMMARY OF THE INVENTION

Thus, an object of the present invention is to provide a novel and improved enterosoluble capsulated medicament with which the effect of the medicine is rapidly exhibited within a well-controlled time after administration regardless of whether the administration of the medicament is after meal or before meal.

Another object of the present invention is to provide a novel and improved method for treating a patient by administrating an enterosoluble medicament in which the exhibition of the effect of the medicine is rapid within a well-controlled time after administration regardless of whether the administration is after meal or before meal.

The inventive enterosoluble medicamental hard capsule is characterized in that the overall specific gravity thereof is at least 1.05 in contrast to the conventional medicamental capsules of which the overall specific gravity never exceeds 1.05. Such an extraordinarily large overall specific gravity of the medicamental capsules is obtained by incorporating a weighting agent into the capsule together with the active ingredient and other conventional additive ingredients. The preferred weighting agent is barium sulfate owing to its large density as a weighting agent as well as to its physiological inertness.

The X-ray examination of the behavior of the inventive capsulated medicament clearly demonstrates the rapid and well-controlled transfer of the capsules into the intestinal canals through the stomach of the patient administrated therewith.

BRIEF DESCRIPTION OF THE DRAWING

FIG. 1 to FIG. 5 are the schematic illustration of the results of the X-ray examination of the behavior of the inventive and conventional capsulated medicaments in the digestive tract periodically undertaken after administration.

DETAILED DESCRIPTION OF THE PREFERRED EMBODIMENTS

Figure 1:
Figure 1:
Figure 1:
Figure 1:
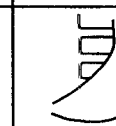
Figure 1:
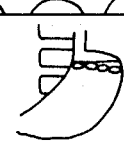
Figure 1:
Figure 1:
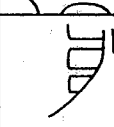
Figure 1:
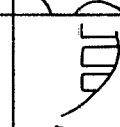
Figure 1:
Figure 1:
Figure 1:
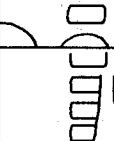
Figure 1:
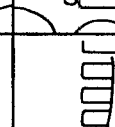
Figure 1:
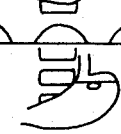
Figure 1:
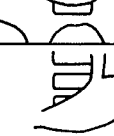
Figure 1:
Figure 1:

On the way of their extensive investigations to find the reason for the undue or irregular delay of the exhibition of the effect of medicine when patients are administrated with enterosoluble capsulated medicaments, the inventors have come to a discovery of very surprising and unexpected facts as described below.

That is, the inventors have conducted a study of the behavior of the enterosoluble hard capsules containing a contrast medium in the digestive tract by X-ray examination. Contrary to the hitherto accepted understanding that an enterosoluble capsule taken by the patient is relatively rapidly transferred from the stomach to the intestinal canals because, when taken before meal, the capsule would be pushed down smoothly to the pyloric region and to the intestinal canals by the mass of foods following the administration of the capsule and, when taken after meal, the capsule would be rapidly intermingled with the ingested foods by the digestive movement of the stomach and behave not differently from the foods to be transferred together to the intestinal canals, the enterosoluble capsules are retained as such in the stomach for as long as several hours after administration floating on the mass of the ingested foods. This unexpected behavior of capsules was observed not only when the administration of the enterosoluble capsule was after meal but also when the enterosoluble capsule was administered before meal followed by ordinary meal within a short time.

The above described unexpected behavior of an enterosoluble capsule in the stomach takes place regardless of the materials of the capsule shells prepared by any one of the above described principles for imparting enterosolubility to the capsules.

As a result of the investigation to discover the reason for the floating behavior of the enterosoluble capsules on the foods in the stomach and to provide a means for preventing this undesirable phenomenon, the inventors have arrived at a conclusion that the overall specific gravity of the capsulated medicament is the key parameter to ensure rapid and smooth transfer of the capsule from the stomach to the intestinal canals. Conventional capsulated medicaments having an overall specific gravity not exceeding 0.7-0.8 were always subject to the undesirable phenomenon of floating on the foods while test capsules prepared by incorporating a weighting agent, e.g. barium sulfate, were rapidly and smoothly transferred from the stomach to the intestinal canals.

The inventors have further conducted experiments with enterosoluble capsules with varied overall specific gravities and established that the overall specific gravity of an enterosoluble capsulated medicament should be at least 1.05 or, preferably, at least 1.10 in order that the rapid and smooth transfer of the capsule is ensured from the stomach to the intestinal canals. When the administrated entersoluble capsule has an overall specific gravity smaller than 1.05, floating of the capsule on the contents of the stomach is always unavoidable regardless of whether the administration is before meal or after meal with remarkable delay of transfer to the intestinal canals. On the other hand, the behavior of an enterosoluble capsule having an overall specific gravity of at least 1.05 or, in particular, at least 1.10 is hardly influenced by the contents of the stomach. Such a weighted capsule rapidly sinks to the bottom of the stomach from where it is smoothly transferred to the intestinal canals through the pyloric region without being disturbed by the contents of the stomach. When the overall specific gravity of an enterosoluble capsule is increased over 1.10, no particular further improvement is obtained in the behavior of the capsule in the stomach and the order of transfer of capsule having various overall specific gravities no longer depends on the overall specific gravity. The time taken for the transfer of the weighted enterosoluble capsules is about the same as conventional enterosoluble tablets and several of the capsules have been transferred to the intestinal canals after about 5 hours from administration.

The above mentioned increased overall specific gravity of enterosoluble capsulated medicaments is readily obtained by use of a weighting agent. Suitable weighting agents include barium sulfate, calcium dihydrogenphosphate, iron oxide, titanium dioxide, calcium sulfate, platinum and the like from the standpoints of not only obtaining sufficient weight but also physiological inertness and non-reactivity with the active ingredient contained in the capsule. It is of course optional to use two kinds or more of these weighting agents in combination. Among the above named ones, the most preferred weighting agent is barium sulfate. These weighting agents are most conveniently incorporated into the capsule together with the active ingredient and other additives but it is optional that they are admixed in advance with the gelatine or other capsule materials before shaping into capsule shells provided that the admixture of the weighting agents has no adverse effect to the moldability of the capsule material.

When the weighting agent is incorporated into the capsule together with the other ingredients, the blend can be in the form of a powder blend or in the form of suspension or paste by use of a suitable suspension medium or an oily base. The oily base suitable for the purpose is exemplified by liquid oils such as sesame oil, olive oil, soybean oil, rapeseed oil, cottonseed oil, linseed oil, castor oil, rice-bran oil, camellia oil, coconut oil, peanut oil, corn oil, poppy oil and the like as well as those fats solid at room temperature but becoming liquid at 37° C. or higher such as cacao butter, cinnamon butter, laurin, beef tallow, hog fat, wool fat and the like. Further, the products obtained from the above oils and fats by hydrogenation, carboxylic acid exchange or acetylation splitting are also suitable and esters of glycerine with a carboxylic acid having from 6 to 30 carbon atoms in a molecule such as glycerine palmitate, glycerine stearate, glycerine myristate and the like may be used. In addition to these oily bases, glycerine and sugar syrup can be used as the base according to the nature of the active ingredient.

It is further optional that the content of the inventive medicamental capsule contains, according to need, various kinds of other conventional additives such as water-soluble additives, e.g. hydroxypropylcellulose of low degree of substitution, carboxymethylcellulose, carboxymethylstarch, lecithine, polyethyleneglycol, Polysolvate 80 and the like, thickners or thioxotropy-imparting agents, e.g. colloidal silica, aluminum stearate and the like, and surface active agents. Rough measures for the amounts of the oily base and the weighting agent are 1.5 to 15 times by weight and up to 15 times by weight of the active ingredient for the former and for the latter, respectively.

The amount of the weighting agent, e.g. barium sulfate, to be incorporated into a capsule is readily calculated from the volume of the capsule, weight of the capsule, amount of the ingredients contained in the capsule other than the weighting agent and the desired overall specific gravity. Assume that a #0 capsule having a weight of 120 mg and a volume of 1.0 ml or 1000 $\mu$l is used to contain 250 mg of an active ingredient, e.g. aspirin, and the desired overall specific gravity of the weighted capsule is 1.10, then the amount of barium sulfate to be incorporated into the capsule is $(1000 \times 1.10) - (120 + 250) = 730$ mg.

When the effective volume of a #0 capsule, which has ordinarily a volume of 1.0 ml, can be reduced by one or other means, the amount of the weighting agent can accordingly be reduced. For example, the usually semispherical cap ends of the capsule shells are flattened so that the effective volume of the capsule is reduced to 0.8 ml, then the necessary amount of the weighting agent would be, the other parameters being the same as above, $(800 \times 1.10) - (120 + 250) = 510$ mg. Similar calculation gives tabulation of the necessary amounts of the weighting agent with varied parameters as shown in Tables 1 and 2 below.

Further calculations were undertaken to obtain tabulations for ternary suspensions composed of aspirin, sesame oil and barium sulfate to just fill the effective volume of a capsule from the true densities of these components. The calculated results of the amounts of sesame oil and barium sulfate in mg are shown in Tables 3 to 6, of which Table 3 is for a #0 capsule containing 250 mg of aspirin with varied effective volumes, Table 4 is for a #0 capsule containing 50 mg of aspirin with varied effective volumes, Table 5 is for #1 and #2 capsules containing 250 mg of aspirin and Table 6 is for #1 and #2 capsules containing 50 mg of aspirin.

TABLE 1

(Amount of weighting agent, mg, with 250 mg of the base ingredient)

| Size of capsule (weight, mg) | | #0 (120) | | | #1 (92) | #2 (78) |
|---|---|---|---|---|---|---|
| Effective volume, ml | 1.0 | 0.9 | 0.8 | 0.72 | 0.60 | 0.44 |
| Overall specific gravity | 0.90 | 530 | 440 | 350 | 278 | 117 | 23 |
| | 1.00 | 630 | 530 | 430 | 350 | 168 | 62 |
| | 1.10 | 730 | 620 | 510 | 422 | 219 | 101 |
| | 1.20 | — | 710 | 590 | 494 | 270 | 140 |
| | 1.30 | — | 800 | 670 | 566 | 321 | 179 |
| | 1.40 | — | — | 750 | 638 | 372 | 218 |
| | 1.50 | — | — | — | 710 | 423 | — |

TABLE 2

(Amount of weighting agent, mg. with 50 mg of the base ingredient)

| Size of capsule (weight, mg) | | #0 (120) | | | #1 (92) | #2 (78) |
|---|---|---|---|---|---|---|
| Effective volume, ml | 1.0 | 0.9 | 0.8 | 0.72 | 0.60 | 0.44 |
| Overall specific gravity | 0.90 | 730 | 640 | 550 | 478 | 317 | 223 |
| | 1.00 | 830 | 730 | 630 | 550 | 367 | 262 |
| | 1.10 | 930 | 820 | 710 | 622 | 419 | 301 |
| | 1.20 | 1030 | 910 | 790 | 694 | 470 | 340 |
| | 1.30 | 1130 | 1000 | 870 | 766 | 521 | 379 |
| | 1.40 | — | 1090 | 950 | 838 | 572 | 418 |
| | 1.50 | — | — | 1030 | 910 | 623 | — |

TABLE 3

(Amounts of sesame oil and barium sulfate, mg, in #0 capsule with 250 mg of aspirin)

| Effective volume, ml | | 1.0 | | 0.9 | | 0.8 | | 0.72 | |
|---|---|---|---|---|---|---|---|---|---|
| Ingredient | | Sesame oil | BaSO$_4$ | Sesame oil | BaSO$_4$ | Sesame oil | BaSO$_4$ | Sesame oil | BaSO$_4$ |
| Overall specific gravity | 0.90 | 634 | 54 | — | — | — | — | — | — |
| | 1.00 | 450 | 180 | 476 | 56 | — | — | — | — |
| | 1.10 | 424 | 305 | 453 | 169 | 481 | 30 | — | — |
| | 1.20 | 399 | 431 | 430 | 282 | 460 | 130 | 485 | 9 |
| | 1.30 | 373 | 557 | 407 | 395 | 440 | 231 | 467 | 99 |
| | 1.40 | 349 | 675 | 385 | 506 | 420 | 331 | 448 | 189 |
| | 1.50 | 324 | 800 | 362 | 619 | 399 | 431 | 430 | 279 |

TABLE 4

(Amounts of sesame oil and barium sulfate, mg, in #0 capsule with 50 mg of aspirin)

| Effective volume, ml | | 1.0 | | 0.9 | | 0.8 | | 0.72 | |
|---|---|---|---|---|---|---|---|---|---|
| Ingredient | | Sesame oil | BaSO$_4$ | Sesame oil | BaSO$_4$ | Swsame oil | BaSO$_4$ | Sesame oil | BaSO$_4$ |
| Overall specific gravity | 0.90 | 594 | 138 | 617 | 23 | — | — | — | — |
| | 1.00 | 568 | 264 | 595 | 136 | 620 | 11 | — | — |
| | 1.10 | 543 | 389 | 572 | 249 | 599 | 112 | — | — |
| | 1.20 | 518 | 514 | 549 | 362 | 579 | 212 | 603 | 90 |
| | 1.30 | 492 | 640 | 526 | 475 | 559 | 312 | 585 | 181 |
| | 1.40 | 466 | 763 | 501 | 586 | 538 | 413 | 567 | 272 |
| | 1.50 | 441 | 889 | 478 | 699 | 518 | 513 | 548 | 362 |

TABLE 5

(Amounts of sesame oil and barium sulfate, mg, in capsules with 250 mg of aspirin)

| Size of capsule Ingredient | | #1 | | #2 | |
|---|---|---|---|---|---|
| | | Sesame oil | BaSO$_4$ | Sesame oil | BaSO$_4$ |
| Overall specific gravity | 1.10 | 290 | 28 | 155 | 0 |
| | 1.20 | 275 | 103 | 183 | 17 |
| | 1.30 | 260 | 178 | 172 | 72 |
| | 1.40 | 244 | 255 | 161 | 126 |
| | 1.50 | 229 | 330 | 150 | 181 |

TABLE 6

(Amounts of sesame oil and barium sulfate, mg, in capsules with 50 mg of aspirin)

| Size of capsule Ingredient | | #1 | | #2 | |
|---|---|---|---|---|---|
| | | Sesame oil | BaSO$_4$ | Sesame oil | BaSO$_4$ |
| Overall specific gravity | 1.00 | 424 | 34 | — | — |
| | 1.10 | 409 | 109 | 312 | 44 |
| | 1.20 | 393 | 184 | 301 | 99 |
| | 1.30 | 378 | 260 | 290 | 154 |
| | 1.40 | 362 | 338 | 279 | 209 |
| | 1.50 | 347 | 413 | 268 | 263 |

Based on the above given results of calculation, several enterosoluble medicamental capsules were actually prepared and the overall specific gravities of them were determined as described below.

Preparation of Weighted Enterosoluble Capsules

Preparation 1. An enterosoluble capsule of #0 size was filled with a uniform mixture of 250 mg of aspirin and 730 mg of barium sulfate to find that the overall specific gravity of the capsule was 1.10.

Preparation 2. A dispersion was prepared by dispersing 50 g of aspirin and 38.8 g of barium sulfate in 54.2 g of sesame oil and an enterosoluble capsule of #0 size was filled with 980 mg of the suspension to find that the overall specific gravity of the capsule was 1.10.

Preparation 3. A suspension was prepared by dispersing 5 g of aspirin and 11 g of barium sulfate in 41 g of sesame oil and an entersoluble capsule of #1 size was filled with 750 mg of the suspension containing 50 mg of aspirin to find that the overall specific gravity of the capsule was about 1.10.

Preparation 4. A pasty mixture was prepared by kenading 25 g of aspirin and 56 g of barium sulfate with 37 g of sesame oil and an enterosoluble capsule of #0 size was filled with 1180 mg of the pasty mixture containing 250 mg of aspirin to find that the overall specific gravity of the capsule was about 1.30.

Preparation 5. A suspension was prepared by dispersing 12.5 g of aspirin, 2.7 g of aluminum stearate and 21.8 g of barium sulfate in 17 g of sesame oil and an enterosoluble capsule of #0 size was filled with 1080 mg of the suspension containing 250 mg of aspirin to find that the overall specific gravity of the capsule was about 1.20.

Preparation 6. A suspension was prepared by dispersing 12.5 g of aspirin and 2.0 g of aluminum stearate in 5.8 g of sesame oil and an enterosoluble capsule of #2 size was filled with 405 mg of the suspension containing 250 mg of aspirin to find that the overall specific gravity of the capsule was about 1.10.

Following are the examples to illustrate the behavior of weighted enterosoluble capsules in the digestive tracts as traced by X-ray examination. The results of the tests including several comparative tests are shown schematically in FIGS. 1 to 5.

EXAMPLE 1

Enterosoluble hard capsules of #0 size were prepared with an enterosoluble cellulose derivative which was a mixed acidic succinyl and aliphatic monoacyl ester of an alkyl- and hydroxyalkyl-substituted cellulose ether and the overall specific gravity of the sealed capsule was adjusted to 0.75 by incorporating a suitable amount of barium sulfate thereinto.

Four healthy subjects, all male and adult, with empty stomach were administrated each with 4 pieces of the above capsules together with 70 ml of water and the behavior of the capsules was traced by means of X-ray examination to give results as illustrated in FIG. 1. As is clear from the figure, all of the capsules had been transferred to the intestinal canals within 1 hour in all of the subjects.

EXAMPLE 2

Each two of enterosoluble capsules having overall specific gravities of 0.75 and 1.25 were prepared in the same manner as in Example 1 and a subject was administrated with these 4 capsules 30 minutes after ordinary meal together with 70 ml of water.

Figure 2:
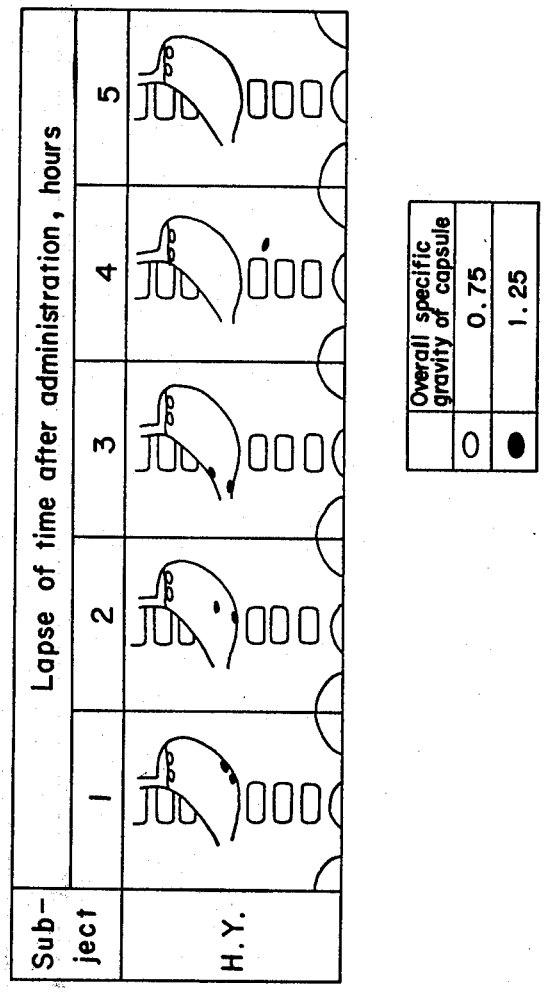

As is illustrated in FIG. 2, the capsules having an overall specific gravity of 0.75 floated on the mass of the ingested foods and remained there until 5 hours after administration. On the other hand, the heavier capsules had passed through the ingested foods within 1 hour after administration to sink to the bottom of the stomach from where they reached the intestinal canals within 3 to 4 hours where they became disintegrated.

EXAMPLE 3

Figure 3:
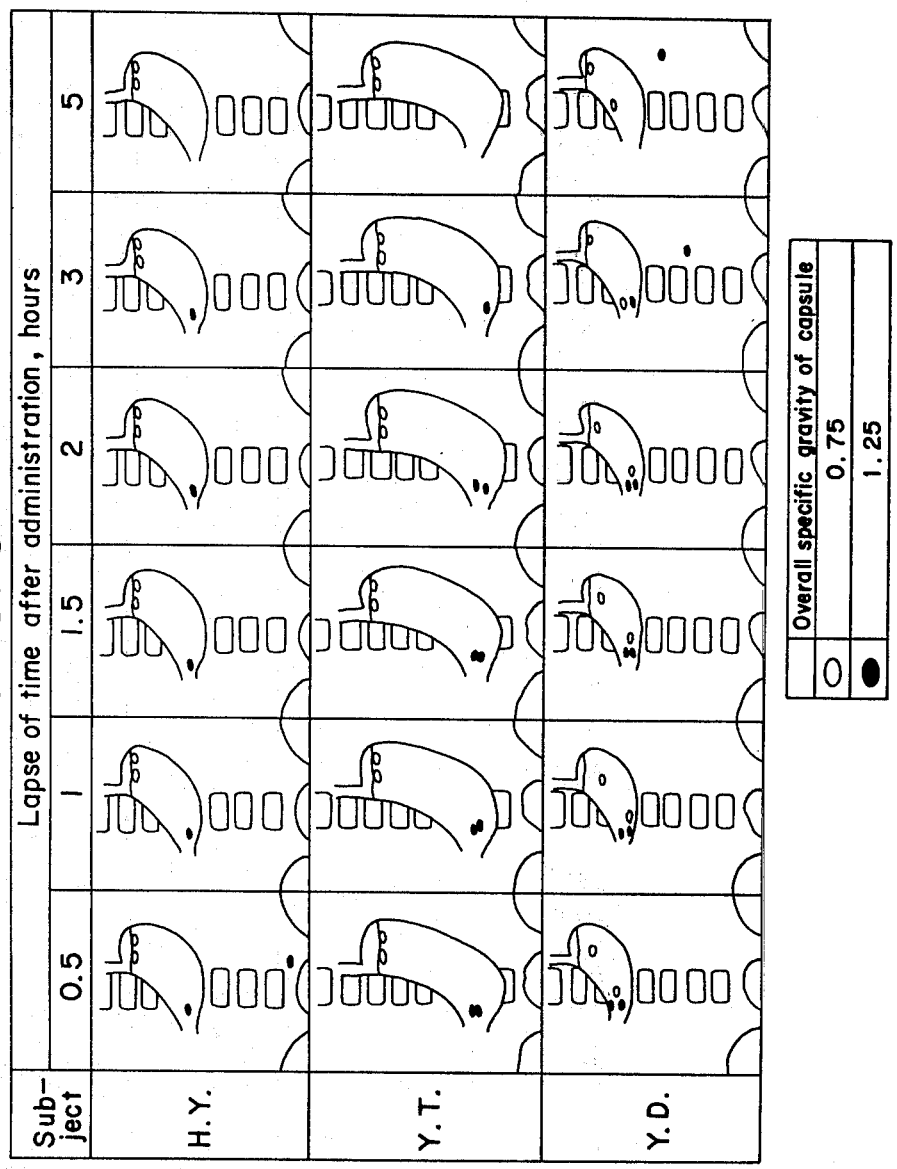

Three subjects with empty stomach were administrated with the same 4 capsules as used in Example 2 10 minutes before an ordinary meal together with 70 ml of water. Despite the administration before meal, the lighter capsules having an overall specific gravity of 0.75 passed upwardly through the ingested foods and were floating 30 minutes after administration in the upper part of the stomach where they remained as such even after 5 hours from administration as is shown in FIG. 3. On the other hand, the heavier capsules having an overall specific gravity of 1.25 rapidly sank to the bottom of the stomach from where they were smoothly transferred to the intestinal canals within 5 hours after administration in all of the subjects as also illustrated in FIG. 3.

EXAMPLE 4

Two subjects were administrated each with 3 pieces of weighted capsules 30 minutes after ordinary meal together with 70 ml of water. The capsules with which the subject H.Y. was administrated had overall specific gravities of 1.00, 1.10 and 1.20, respectively, while the capsules with which the subject Y.D. was administrated had overall specific gravities of 1.00, 1.05 and 1.20, respectively.

Figure 4:
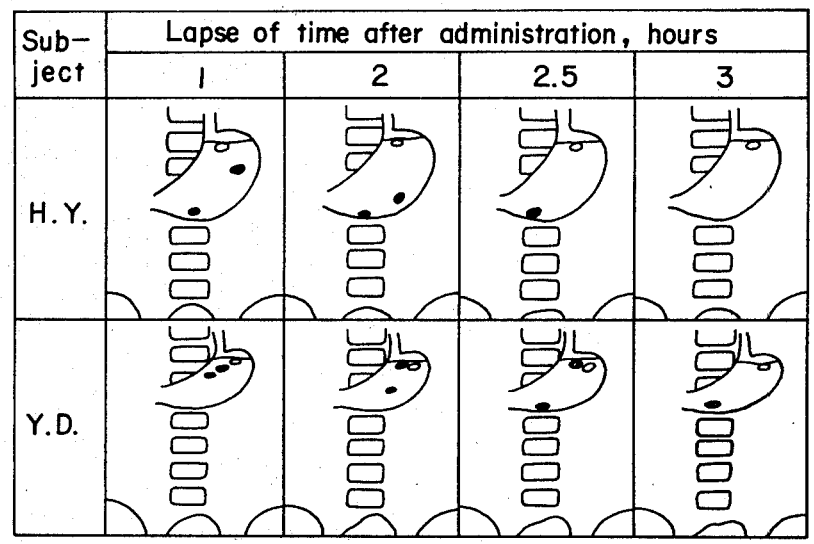

As is illustrated in FIG. 4, the lightest capsule in the subject H.Y. floated in the upper part of the stomach where it remained as such even 3 hours after administration while the heavier two capsules rapidly reached the bottom of the stomach from where they were smoothly transferred to the intestinal canals.

In the subject Y.D., the lightest capsule remained in the upper part of the stomach even after 3 hours from administration while heavier two capsules duly reached the bottom of the stomach.

EXAMPLE 5

Two subjects were each administrated 30 minutes after ordinary meal with three enterosoluble capsules having overall specific gravities of 1.10, 1.20 and 1.30, respectively, and two enterosoluble tablets having a specific gravity of 1.42 together with 70 ml of water. As is illustrated in FIG. 5, all of the capsules, having overall specific gravities of at least 1.10, rapidly reached the bottom of the stomach and several of them had been transferred to the intestinal canals 5 hours after administration with no particular order of transfer with the difference in the overall specific gravity noteworthy to mention. Their behavior was also almost identical with the enterosoluble tablets administrated in the same time.

What is claimed is:

1. A weighted, enterosoluble, mixed acidic succinyl and aliphatic monoacyl ester of an alkyl and hydroxylalkyl substituted cellulose ether coated and sealed hard gelatin coated two-piece capsule shell-encapsulated medicament suspended in a material selected from the group consisting of sesame oil, olive oil, soybean oil, rapeseed oil, cottonseed oil, linseed oil, castor oil, ricebran oil, camellia oil, coconut oil, peanut oil, corn oil, poppy oil, cacao butter, cinnamon butter, laurin, beef tallow, hog fat, wool fat, products obtained from said oils and fats by hydrogenation, carboxylic acidic exchange or acetylation splitting and esters of glycerine with a carboxylic acid having from 6 to 30 carbon atoms in a molecule; said capsule having the usual semi-spherical cap ends of the capsule shells flattened so that the effective volume of the capsule is reduced and being weighted with a material selected from the group consisting of barium sulfate, calcium dihydrogenphosphate, iron oxide, titanium dioxide, calcium sulfate, and platinum, either in the capsule shell or in the capsule fill and having an overall specific gravity of at least 1.05.

2. A barium sulfate weighted enterosoluble mixed acidic succinyl and aliphatic monoacyl ester of an alkyl and hydroxyalkyl substituted cellulose ether coated and sealed hard gelatin telescoping two-piece capsule shell-encapsulated medicament suspended in sesame oil and having the usual semispherical cap ends of the capsule shells flattened so that the effective volume of the capsule is reduced, and being weighted with barium sulfate either in the capsule shell or in the capsule fill and having an overall specific gravity of at least 1.05.

* * * * *